United States Patent
Goossen et al.

(10) Patent No.: US 12,016,711 B2
(45) Date of Patent: Jun. 25, 2024

(54) MULTI-SPECTRAL X-RAY IMAGING USING CONVENTIONAL EQUIPMENT

(71) Applicant: KONINKLIJKE PHILIPS N.V., Eindhoven (NL)

(72) Inventors: André Goossen, Eldena (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 238 days.

(21) Appl. No.: 17/637,954

(22) PCT Filed: Aug. 21, 2020

(86) PCT No.: PCT/EP2020/073540
§ 371 (c)(1),
(2) Date: Feb. 24, 2022

(87) PCT Pub. No.: WO2021/037749
PCT Pub. Date: Mar. 4, 2021

(65) Prior Publication Data
US 2022/0273252 A1    Sep. 1, 2022

(30) Foreign Application Priority Data

Aug. 27, 2019  (EP) .................................... 19193702

(51) Int. Cl.
*A61B 6/40*   (2024.01)
*A61B 6/00*   (2024.01)
*A61B 6/04*   (2006.01)

(52) U.S. Cl.
CPC ............ *A61B 6/405* (2013.01); *A61B 6/0487* (2020.08); *A61B 6/4452* (2013.01); *A61B 6/5264* (2013.01)

(58) Field of Classification Search
CPC ..... A61B 6/405; A61B 6/0487; A61B 6/4452; A61B 6/5264; A61B 6/482; A61B 6/5258; A61B 6/032
See application file for complete search history.

(56) References Cited

U.S. PATENT DOCUMENTS

| 7,480,365 B1 | 1/2009 | Topfer |
| 2012/0020454 A1 | 1/2012 | Murakoshi |

(Continued)

FOREIGN PATENT DOCUMENTS

| JP | 2008023241 A | 2/2008 |
| WO | WO2015032664 A1 | 3/2015 |
| WO | WO2016087394 A1 | 6/2016 |

OTHER PUBLICATIONS

PCT International Search Report, International application No. PCT/EP2020/073540, Feb. 4, 2021.

(Continued)

*Primary Examiner* — David P Porta
*Assistant Examiner* — Casey Bryant
(74) *Attorney, Agent, or Firm* — Larry Liberchuk (57) ABSTRACT

An X-ray imaging apparatus (XI) including an X-ray source (XS) with a cathode (C) and an anode (A). The source (XS) is to generate an X-radiation beam (XB). An X-ray detector (XD) detects the X-radiation after interaction with an imaged object (OB). The beam (XB) has different spectra on its anode side (AS) and cathode side (CS) caused by the heel effect when the X-ray source (XS) is in operation. -ray imaging apparatus (XI) has a heel-effect-harnessing (HH) mechanism configured to cause a pixel (PX) of the detector (XD) to be alternately exposed to both, the anode side (AS) and the cathode side (CS) of the beam (XB).

10 Claims, 8 Drawing Sheets

(56) References Cited

U.S. PATENT DOCUMENTS

| | | | | |
|---|---|---|---|---|
| 2013/0114871 A1* | 5/2013 | Berkus | ............... | G06T 11/008 |
| | | | | 382/131 |
| 2015/0125055 A1 | 5/2015 | Gao | | |
| 2016/0314568 A1 | 10/2016 | Virshup | | |
| 2019/0244397 A1* | 8/2019 | Ikhlef | ............... | G06T 11/006 |
| 2022/0273252 A1* | 9/2022 | Goossen | ............ | A61B 6/4452 |

OTHER PUBLICATIONS

Alvarez R.E. et al., "Energy-Selective Reconstructions in X-ray Computerized Tomography", Phys. Med. Biol., 1976, vol. 21, No. 5, pp. 733-744.

* cited by examiner

MULTI-SPECTRAL X-RAY IMAGING USING CONVENTIONAL EQUIPMENT

FIELD OF THE INVENTION

The invention relates to X-ray imaging apparatuses, to methods of X-ray image acquisition, to a computer program element, to a computer readable medium, and to the use of the heel effect in X-ray imaging.

BACKGROUND OF THE INVENTION

X-ray imaging remains a mainstay for a vast range of diagnostic and therapeutic tasks in medical imaging.

Traditional X-ray imaging is energy integrating in that spectral information in the X-ray radiation is not exploited. X-ray detectors are used merely to detect the integrated energy as line integrals to compute an attenuation image. This traditional energy integrating X-ray imaging does not usually allow for material discrimination. For instance, it may not be possible to distinguish whether a certain attenuation is due to a small thickness of a high density material or to a larger thickness of a material of lower density. In both of these circumstances the same attenuation would be observed in energy integrating conventional X-ray imaging.

Spectral X-ray imaging changes this in that it harnesses the spectral information in the received x-radiation as detected at the X-ray detector. Spectral X-ray imaging allows to compute material specific "maps", that is, images where contrast is conferred by a specific material type. Spectral X-ray imaging may also be used to compute mono-energetic images as another application.

However, spectral X-ray imaging calls for new investments as existing X-ray imagers are usually not suitable for spectral imaging. Dedicated hardware is required such as dual layer detectors, fast switching X-ray sources, dual X-ray source imagers, etc.

SUMMARY OF THE INVENTION

There may therefore be a need for alternative ways to perform spectral X-ray imaging.

The object of the present invention is solved by the subject matter of the independent claims where further embodiments are incorporated in the dependent claims. It should be noted that the following described aspect of the invention equally applies to the methods of X-ray image acquisition, to the computer program element and to the computer readable medium.

According to a first aspect of the invention there is provided an X-ray imaging apparatus including an X-ray source with a cathode and an anode, configured to generate an X-radiation beam, and an X-ray detector for detecting the X-radiation after interaction with an imaged object, the beam having different spectra on its anode side and cathode side caused by the heel effect when the X-ray source is in operation, and a heel-effect-harnessing mechanism configured to cause a pixel of the detector to be alternately exposed to both, the anode side and the cathode side of the beam, by changing the imaging geometry by controlling actuators in concert with the timing of read-out activity at the data acquisition unit, said actuators acting on at least one of the X-ray source, a patient examination table and the detector.

The proposed approach allows using existing X-ray imagers without additional hardware components to perform spectral imaging.

The heel effect harnessing mechanism includes in embodiments only standard components such as the X-ray source and the X-ray detector. The components are operated through a control unit in coordination to implement a new imaging protocol. The control unit may be an existing one that can be reprogrammed to implement the new protocol. An existing energy integrating X-ray imager may hence be operated in spectral imaging mode. No new hardware components are required in these embodiments.

In more detail, in embodiments the heel effect harnessing mechanism changes an imaging geometry so that each geometrical pixel is exposed in sequence to different portions of the beam, the anode side and cathode side, and hence to different spectra thanks to the heel effect.

In embodiments, the heel-effect-harnessing mechanism causes a relative motion between the object and the X-ray beam.

In embodiments, the said motion is caused by motion of at least a part of a support on which the imaged object resides during imaging, and/or or is caused by a motion of the X-ray source.

In embodiments, the motion of the X-ray source is transversal and/or is rotatory so that respective positions of the anode and cathode are changed, in particular and in embodiments, are (ex)changed.

In embodiments, the heel-effect-harnessing mechanism causes a motion of the or a support and/or the X-ray source so as to increase a distance between the X-ray source and the object.

In embodiments, a plurality of pixels is so exposed, to obtain two sets of intensity readings for the plurality of pixels, at least one for each of the two spectra, the apparatus further including a spectral imaging processor configured to compute spectral imagery for the object based on the two sets of intensity readings.

Although the above described embodiments can be used without additional hardware, certain such additional hardware is still in envisaged in alternative embodiments to which reference is now made. Specifically, according to another aspect there is provided an X-ray imaging apparatus including an X-ray source, configured to generate an X-radiation beam and an X-ray detector for detecting the X-radiation after interaction with an imaged object, and a movable filter arranged between the X-ray source and the object and movable by a control unit so as to change at least locally a spectrum of the beam into a first and second spectrum, to thereby cause a pixel of the detector to be alternately exposed to X-radiation at the two spectra.

The additional hardware is envisaged in the form of the filter element. However, this filter is cheaper and much easier to mount/retrofit than the above described dedicated spectral hardware options which are expensive solutions.

In embodiments, the filter includes sub-elements including respectively a different material, wherein, caused by the filter motion, at least two of the sub-elements are brought, alternately, one at a time, into (perspective) registry with the pixel.

The two material are to cause different spectral modulation. Combinations envisaged include Al und Cu or Al und a polymer such as PE. One of the elements may be formed as a void in which case air is one of the materials.

In embodiments, the sub-elements are arranged in a checkerboard pattern.

In another aspect there are provided related method in including a method of image acquisition for an X-ray imaging apparatus, the apparatus including an X-ray source with a cathode and an anode, configured to generate an X-radiation beam, and an X-ray detector for detecting the X-radiation after interaction with an imaged object, the beam having different spectra on its anode side and cathode side caused by the heel effect when the X-ray source is in operation, the method comprising:

alternately exposing a pixel of the detector to both, the anode side and the cathode side of the beam, by changing the imaging geometry by controlling actuators in concert with the timing of read-out activity at the data acquisition unit, said actuators acting on at least one of the X-ray source, a patient examination table and the detector.

In another aspect there is provided a method of image acquisition for an X-ray imaging apparatus, the apparatus including an X-ray source to generate an X-radiation beam and an X-ray detector for detecting the X-radiation after interaction with an imaged object, the method comprising:

alternately exposing a pixel of the detector to X-radiation at first and second spectrum by moving a movable filter arranged between the X-ray source and the object so as to change at least locally a spectrum of the beam into the first and second spectrum.

In embodiments the alternate exposure causes two measurement values to be detected at different spectra at the pixel, and wherein the method further comprises processing the two measurement values by a spectral imaging algorithm.

In embodiments the spectral imaging algorithm is implemented as a machine learning algorithm.

In another aspect there is provided a computer program element, which, when being executed by at least one processing unit, is adapted to cause the processing unit to perform any of the above described methods.

In another aspect there is provided a computer readable medium having stored thereon the program element.

In another aspect there is provided the use of the heel effect to achieve spectral X-ray imaging.

Definitions

"user" relates to a person, such as medical personnel or other, operating the imaging apparatus or overseeing the imaging procedure. In other words, the user is in general not the patient.

"object" is used herein in the general sense to include animate "objects" such as a human or animal patient, or anatomic parts thereof but also includes inanimate objects such as an item of baggage in security checks or a product in non-destructive testing. However, the proposed system will be discussed herein with main reference to the medical field, so we will be referring to the "object" as "the patient" and the location of interest ("ROI"), being a particular anatomy or group of anatomies of the patient.

"Motion" as used herein includes a change in position and/or orientation relative to a world-coordinate system.

"(filter) Material" as used herein includes air, so one of the filter elements may be formed as an aperture. Exactly two different material types may be sufficient herein as these may be arranged spatially in a spatially alternating fashion such as in a checkerboard manner of plural sub-filter elements. One dimensional layouts may also be envisaged instead, and so are filter layouts with more than two material types. The different materials are to cause different spectral modulation.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figure 1:
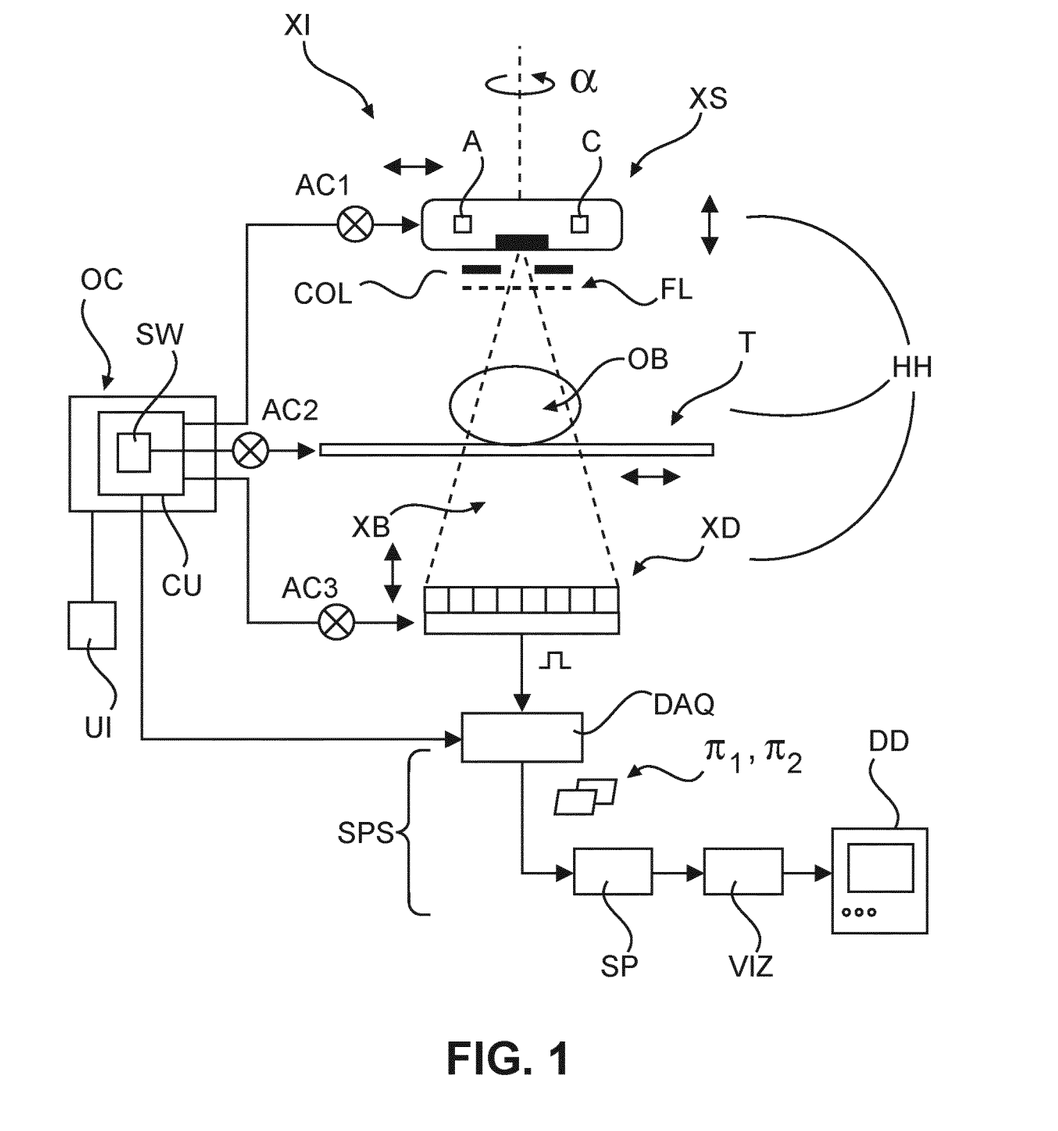
FIG. 1 shows a schematic diagram of components of an X-ray imaging apparatus.

With reference to FIG. 1, this is a schematic diagram of an X-ray imaging apparatus XI. Embodiments for this include a C-arm imaging apparatus, a CT scanner, a mammography apparatus, a dental X-ray imager, or a radiography apparatus, or other, configured to acquire an X-ray image of an object OB.

In broad terms, components of the X-ray imaging apparatus XI include an X-ray source XS and an X-ray sensitive detector XD. In use, the object OB is positioned in an examination region within the X-ray source XS and the X-ray detector XD. To facilitate this, there is in some embodiments provided an examination table T on which the patient OB resides during the imaging.

As envisaged herein, some or all of the mentioned components are used in a new imaging protocol, administered by a control unit CU, to allow spectral imaging. No additional hardware components are required for this in embodiments, and this will be discussed more fully below after explaining operation of the components in more detail.

In use, the X-ray source XS is energized to produce an X-ray beam XB which traverses the examination region, and hence at least a region of interest of the object OB. The X-radiation interacts with matter (e.g., tissue, bones, etc.) of the object OB. After interaction, the radiation impinges on the X-ray detector XD.

The impinging X-radiation is detected by the detectors XD as intensities in the form of electrical signals. The electrical signals are converted by suitable conversion circuitry in a data acquisition unit DAQ into numeric image values which may then be processed into X-ray images by a signal processing sub-system SPS. The signal processing sub-system SPS includes a spectral image processor SP that may be used when the imager is requested by the user, through a suitable user interface, to operate in spectral imaging mode. For example, the user interface may include a button or a touch screen widget in a display associated with the operator console. The spectral image processor SP implements a desired spectral imaging algorithm, such as material decomposition, material mapping, mono-energetic imagery, material cancellation image, effective atomic number image and electron density image etc. Each of these types of imagery will be referred to herein as "spectral imagery/image" See for instance "Energy-selective Reconstructions in X-ray Computerized Tomography" by R E Alvarez et al, published in *Phys. Med. Biol.*, 1976, vol 21, No 5, pp 733-744.

In general, spectral (or multi-energy) imaging utilizes the two intensity readings to resolve the photoelectric and Compton contribution that consists of the mass attenuation coefficients of a scanned material and then identify an unknown material by its value of photoelectric and Compton contribution. This approach is well-suited with materials such as iodine that have a k-edge energy close to a mean value of a diagnostic energy range. Because any two linearly independent sums of two basis functions span the entire attenuation coefficient space, any material can be represented by a linear combination of two other materials, generally referred to as basis materials, such as water and iodine.

The spectral X-ray images are capable of representing details of the internals of the imaged object OB, in particular the presence of different material etc. This can help in diagnosis and therapy or other examination of the imaged object OB. Suitable visualization software may then be used in a visualizer VZ to effect display of the spectral imagery on one or more display devices DD, such as monitors, etc. The images may also be stored in repository or may be processed further otherwise.

Figure 2:
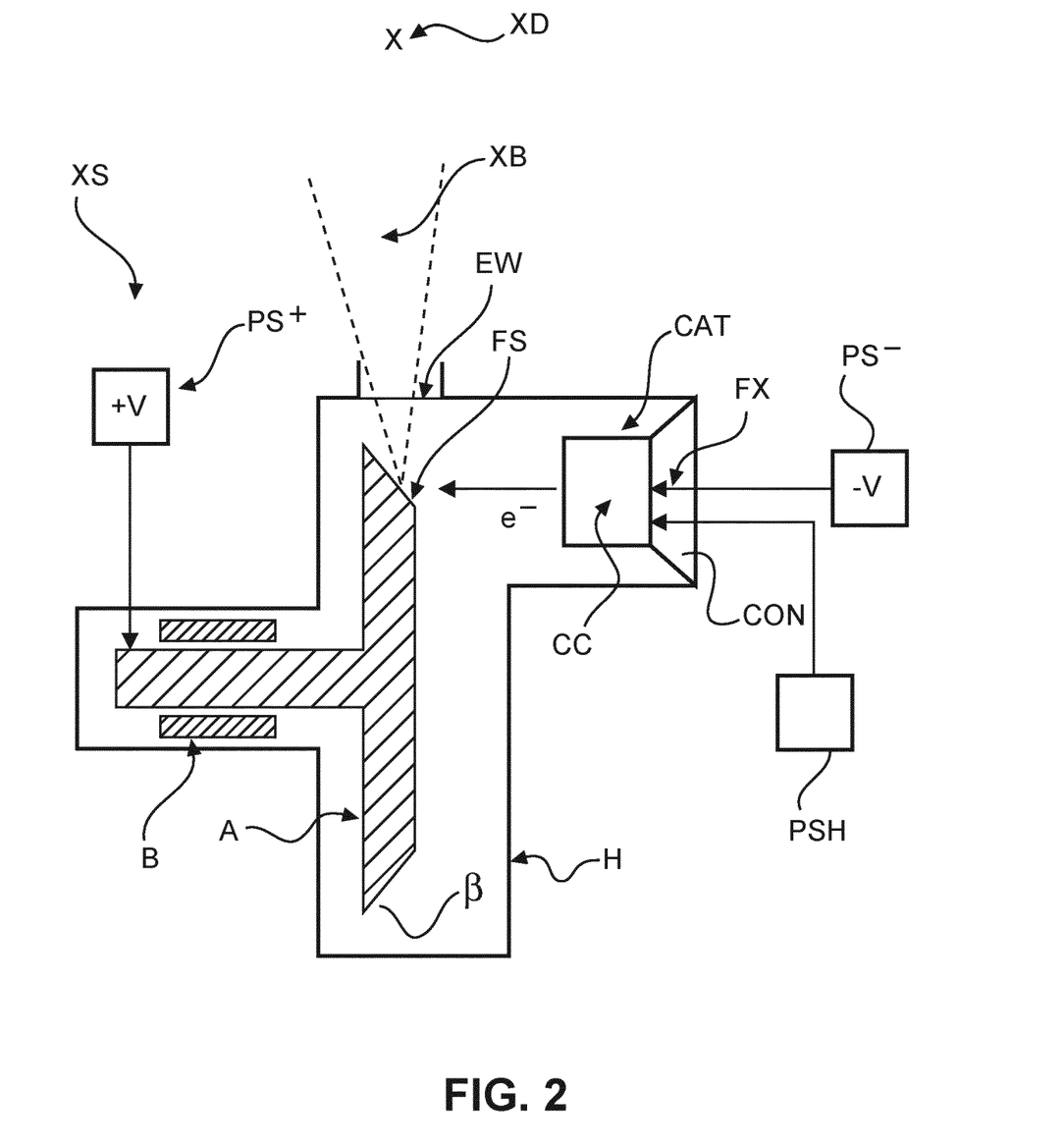
FIG. 2 shows a schematic cross-sectional view of an X-ray source.

FIG. 2 is schematic sectional view of the X-ray source XS. Broadly, the X-ray source XS includes a pair of electrodes, an anode A and a cathode C. A high voltage electrical potential is established between the cathode C and the anode A. This can be done as shown in the FIG. 2 by applying a negative voltage to the cathode C and a positive voltage to the anode A by connecting the cathode and the anode to suitable electrical power supplies $PS^+, PS^-$. Suitable electrical connections CON are provided for this purpose at the source XS. In use, the anode A and cathode C are held at a high voltage potential (referred to herein as "the tube voltage" or the "operation voltage") of about 150 KV relative to ground.

The cathode C and the anode A are arranged spatially in opposing relationship in a housing H to define a driftway between the cathode C and the anode A. The anode A and the cathode C and the driftway are encased in an evacuated glass tube (not shown) inside the housing H.

Preferably, but not necessarily, the X-ray source XS is of the rotary type where the anode is arranged as a disc (shown in cross sectional side view in FIG. 2) which is rotatably journaled in suitable bearing B and driven by an electric motor suitably powered. X-ray sources with stationary anodes are also envisaged.

The cathode C includes an emitter (not shown). An electric current (referred to herein as "emitter current") is generated by a power source PSH. The emitter current is passed through the emitter during use. It will be understood, that the three power sources PSH, $PS^-$, $PS^+$ are shown in FIG. 2 as separate, independent entities and this is indeed envisaged in some embodiments. However, this is not to exclude herein alternative embodiments where some or all of the mentioned power sources are integrated into a single power source. A positioning implement such as a cathode cup CC is arranged to hold the emitter at a distance from a fringe portion of the anode A. The fringe portion may be formed as a beveled edge, in particular when the anode is of the rotary type as shown in FIG. 2. The bevel angle β is usually around 1520 but other bevel angles are also envisaged, such as for example 9°, 12°, 15°, 18°, or any other. When the emitter current is applied, the emitter heats up to a temperature of about 2400° and electrons are boiled off the emitter's surface in thermic emission.

Because of the high potential difference +V,−V between the cathode C and the anode A, the boiled off electrons form an electron beam which is accelerated towards the anode A and impacts at the focal spot FS on the surface of the anode.

In case of the rotatory anode, the focal spot is located on the beveled edge of the anode disc. It will be understood, that, due to the rotation, the focal spot FS traces out a track around the edge of the anode disc AN. The anode AN is formed from a high density material such as Molybdenum, Tungsten or other high-Z metal/material.

When impacting at the focal spot FS, the electron beam decelerates and this energy drop is transformed partly into heat and partly (around 1%) into the X-radiation beam XB which radiates away from the focal spot FS.

The housing H is radiation-blocking, for instance by having a leaden (or other suitable high Z material) layer to prevent the X-radiation from escaping outside the housing, safe for an egress window EW formed from non-radiation opaque material such as glass. The X-radiation beam XR generated inside the X-ray source XS egresses then, essentially undisturbed, through the egress window EW to propagate towards the detector XD (whose relative position is indicated with an "X" in FIG. 2).

Downstream the X-ray source XS, an optional collimator COL may be arranged to form the X-radiation into a directed beam XB having a desired, in general divergent, shape such as cone-beam, fan-beam. Alternatively, more conventional parallel beam geometry is also envisaged herein.

Overall control of the imaging procedure is through user operable computerized operator console OC. The control unit CU, which may be integrated into the operator console OC, controls interaction of the various components and allows selection of operation settings such as cathode voltage, anode current etc. In general, the control unit controls the manner of irradiation by the X-ray beam XB of object OB and detector XD.

Some or all of the components may be movable in motions through respective actuators AC1-AC3 to realize different imaging geometries. The term "imaging geometry" as used herein describes the spatial-geometrical relationship between the X-ray beam XB and the object OB to be imaged and/or the detector XD position/orientation.

Actuators AC1-AC3, through which the imaging geometry can be changed, are controlled by the control unit CU, either automatically or by a user. In one embodiments, one actuator AC1 allows translating the X-ray source XS parallel to the object OB to be imaged and/or parallel to the examination table T. Translation of source may be along one or two spatial dimensions in a plane.

In addition or instead, the imager IX may allow further degrees of freedom. Specifically, in embodiments, the X-ray source itself may be rotatable by actuator AC1 (or by a different actuator) around a rotation axis that passes through the drift way between the anode A and the cathode C towards the X-ray detector XD. In embodiments, the rotation axis passes through the anode, in particular through the focal spot, towards the X-ray detector XD as indicated in FIG. 1. Positions or orientations of the anode and cathode with respect to a world co-ordinates system can thus be changed continuously or in steps by 90° or in any other angular increments. In other words, with a rotation axis passing through the driftway between anode and cathode, a rotation by 180° would exchange the positions of the anode A and the cathode C as shown in side elevation view of FIG. 1.

The rotation axis of the rotatable X-ray source may pass in other embodiments instead through the cathode C. In case where the rotation axis passes though the anode A or cathode C respectively, one of the respective electrode changes its orientation whilst the other electrode changes orientation and position.

In addition or instead to any of the above mentioned degrees of freedom, the examination table T may be translatable in a single or preferably in two dimensions in a plane. It is not required for the whole table to be translated. For present purposes it may be enough for a part of the table, eg; the support surface of the table on which the patient resides, to be translatable through actuator AC2.

An additional actuator AC3 may be used to change the SID ("source to image distance"), that is, the distance along the optical axis OX (not shown in FIG. 1 but shown in FIG. 6D) between the detector XD and the focal spot FS of the X-ray source XS.

Instead of using three separate actuators as discussed above, fewer or more may be used. A single or two actuators may be used in embodiments that operate through a suitable gearing system so that all of the above mentioned motions can be effected.

Figure 3:
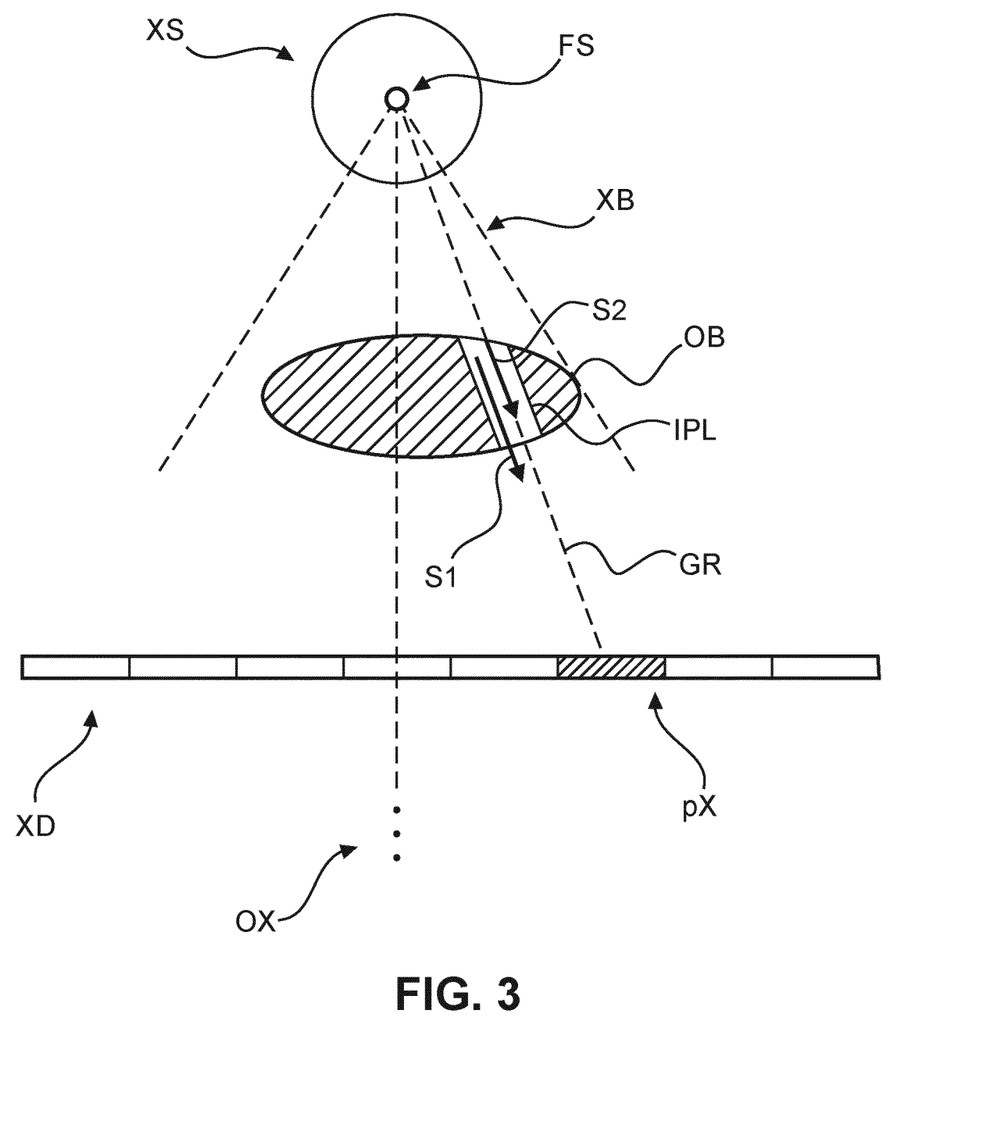
FIG. 3 illustrates spectral X-ray imaging as envisaged herein.

Turning now in more detail to the spectral imaging capability of the X-ray imager XI as proposed herein, reference is now made to FIG. 3. The X-ray beam XB can be conceptualized as a bundle of geometrical rays GR (only one is shown in elevation view of FIG. 3) that emanate from the focal spot FS passing through the object OB to be imaged and terminate in a pixel position. In this sense each geometrical ray has associated thereto a specific pixel. This pixel position may be referred to herein as the geometrical pixel position which may likewise be denoted herein as "GR" but this is to be distinguished from a specific detector pixel position PX.

Along each geometrical ray X-ray photons are travelling and interact with the object and are then detected at the detector PX. The distribution of energy among the photons travelling along each of the geometrical rays defines a local ray spectrum. Different groups of the geometrical rays, with their respective photons travelling therealong, define different beam portions, each portion having a certain local spectrum as function of the different local ray spectra.

Each geometrical ray GR intersects the object to be imaged in an in-tissue path length IPL. For spectral imaging it has to be ensured that each in-tissue path length in the region of interest is traversed or exposed to beam portions of different spectra. The different spectra are indicated in the Fig. as arrows S1, S2 of different lengths. This exposure should occur in sequence so that exposure is first to a radiation having first spectrum S1 and then to radiation photons having a second spectrum S2. These sequential exposures at different spectra will be referred herein as "multi-spectral (X-ray) exposure".

The respective intensity readings at the different spectra need to be read out and registered separately at the respective pixel PX associated with the geometrical ray and hence in-tissue path length of interest. It is proposed herein to change the imaging geometry by controlling the actuators in concert with the timing of read-out activity at the data acquisition unit DAQ to achieve a respective multi-spectral exposure for each pixel of interest. More specifically, it is proposed herein to program the control unit CU to implement a spectral multi-shot imaging protocol that harnesses the heel effect to achieve multi-spectral exposure per geometrical pixel GR/in-tissue path length IPL.

A "shot" as used herein is defined as a discrete period of exposure to x-radiation that may be interrupted and separated in time from a previous or follow-up shot by switching off the X-ray source, applying a switch grid voltage to interrupt the electron beam and/or by closing the collimator or any other suitably quick exposure control scheme. At least two shots per in-tissue path length or geometrical pixel position GR are envisaged herein to ensure the multi-spectral X-ray exposure. The control unit CU is further operative to co-ordinate the read-out sequencing in the read-out circuitry of the data acquisition unit DAQ when capturing the respective exposures at the different spectra.

Figure 4:
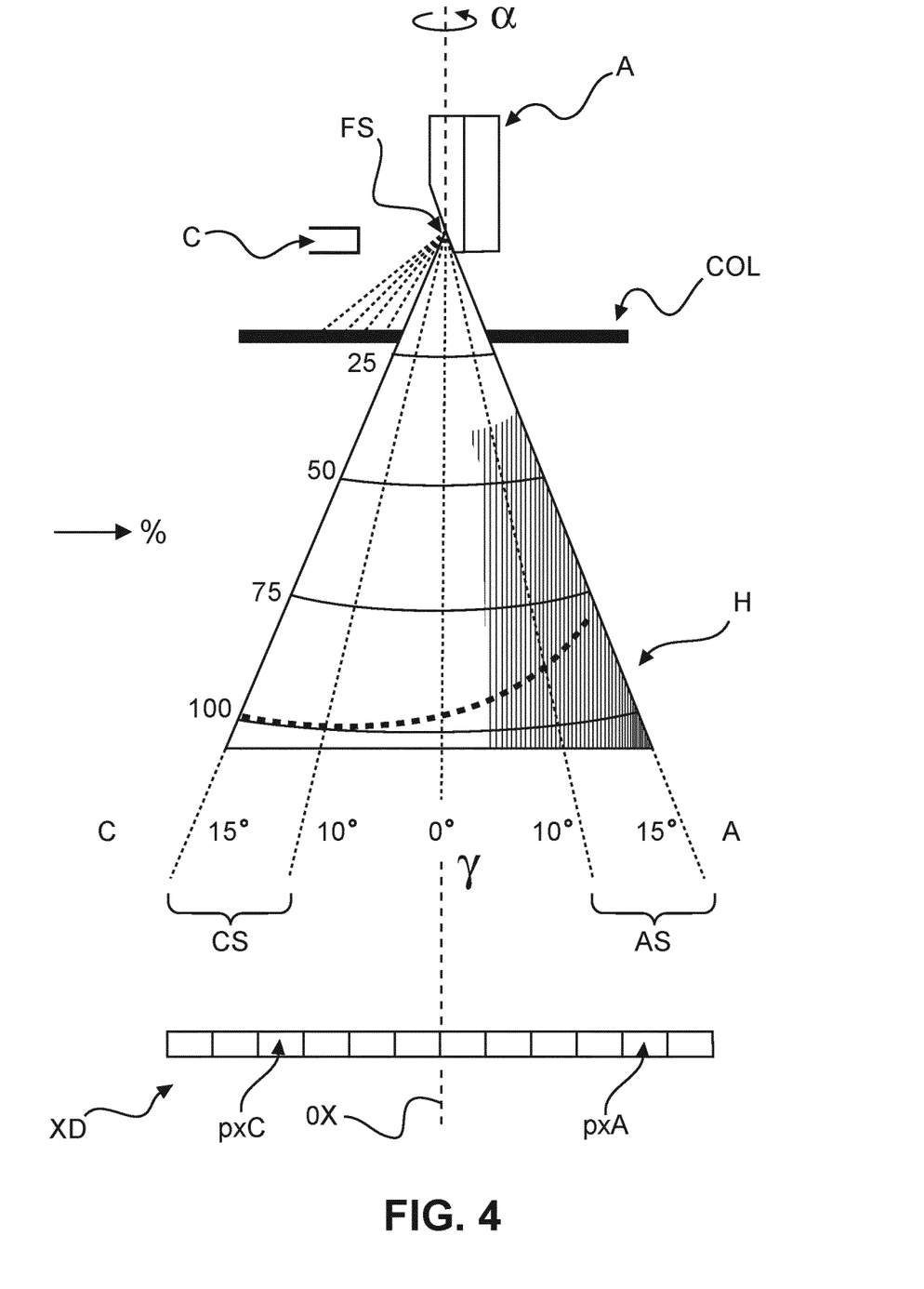
FIG. 4 shows an illustration of the heel effect.

Reference is now made to FIG. 4 to briefly illustrate the heel effect. The distribution of spectra in X-ray beam XB is anisotropic due to the heel effect. The portions of the beam that are closer to the anode and that have a take-off angle γ larger than the bevel angle β of the anode, need to pass through more anode material and hence experience modulation of their spectra. There is also an intensity modulation. The spectral and intensity modulations are illustrated in FIG. 3 by a darker shading at the anode side AS compared to the lighter or no shading at the cathode side CS of the beam XB.

The change in spectra from the cathode side to the anode side is not across a hard boarder, but occurs gradually and the spectral modulation sets in at about a set-off-angle that corresponds to the bevel angle β of the anode. In the example shown in FIG. 4, the bevel angle is 15° and, correspondingly, from a take-off angle larger than 1520 at the anode side, there is a markedly different spectrum as compared to the portion of the beam at the cathode side, shown here at from about 0° (which corresponds to the optical axis OX) to about 15° angulation towards the cathode.

A pixel pxC positioned on the cathode side of the beam will hence experience a different spectrum than an anode side pixel pxA. In other words, the heel effect, which is usually compensated and considered a nuisance, is used herein as a source for multiple spectra exposure to implement spectral imaging.

Figure 5:
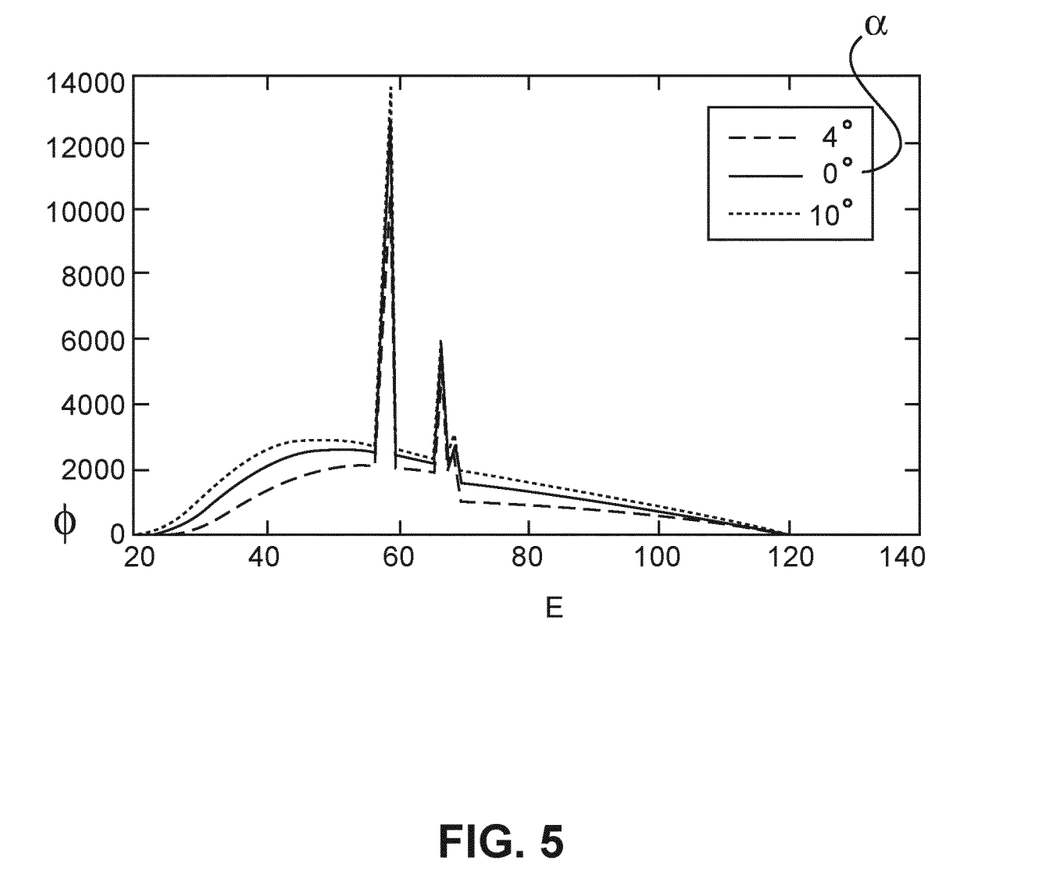
FIG. 5 shows different spectra due to the heel effect as a function of take-off angle.

FIG. 5 is an illustration of the different spectra due to the heel effect. FIG. 5 illustrates spectral graphs where flux Φ is graphed versus energy E. Three spectra are shown: one for the central ray at 0°, one (in dashed line) for a take-off angle of about 4° and one for a take-off angle at about 10° (shown in a dashed-dotted line). The spectrum at 10° take-off angle is anode-side relative to the 4° take-off angle which is relatively more cathode side.

The proposed control unit CU operates preferably and solely with conventional components of the X-ray imager XI to implement a heel harnessing mechanism HH for spectral imaging purposes. The heel harnessing mechanism HH allows an operator to produce spectral imaging with a conventional X-ray imager, preferably without using any additional hardware components.

Reference is now made first to FIG. 6 where different embodiments for the heel effect harnessing mechanism HH are described. Broadly, the heel effect mechanism HH as envisaged herein uses the heel effect, and hence different spectra of different portions of the X-ray beam, to expose in sequence a given pixel to said different spectra. This is done by changing the imaging geometry in concert with DAQ read-out timing, to ensure that each pixel of interest receives the multi-spectral exposure. The control unit CU operates to change the imaging geometry, triggers the appropriate shots and coordinates proper signal capture at read-out circuitry in DAQ to ensure each geometrical pixel position (and hence in-tissue path length) is properly associated with intensity measurement at least two different spectra. In embodiments, it is also ensured that the CU keeps track of which two spectra each pixel is exposed to. The spectral processing by the spectra imaging processor SP will be explained in more detail below.

Figure 6A:
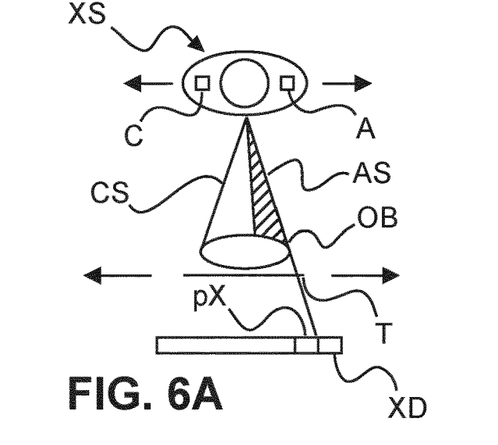
FIG. 6 shows different embodiments of a heel harnessing mechanism usable in an X-ray imaging apparatus.

Turning now first to the hardware aspects of the harnessing mechanism HH, reference is now made to FIG. 6A. In this embodiment the X-ray source and/or the table is moved in a translational movement to essentially scan the object to ensure that each in-tissue-path length is exposed in sequence, at least once, to the anode side portion of the beam AS and to the cathode side of the beam, respectively.

Figure 6B:
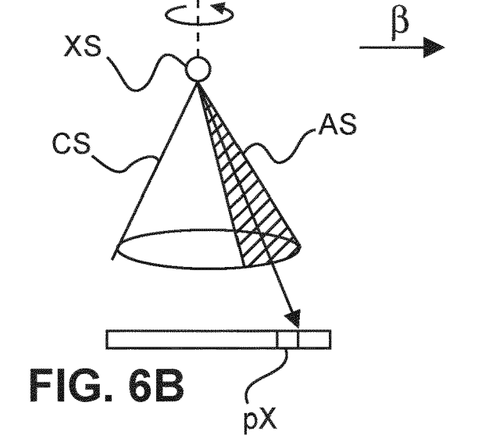
Figure 6C:
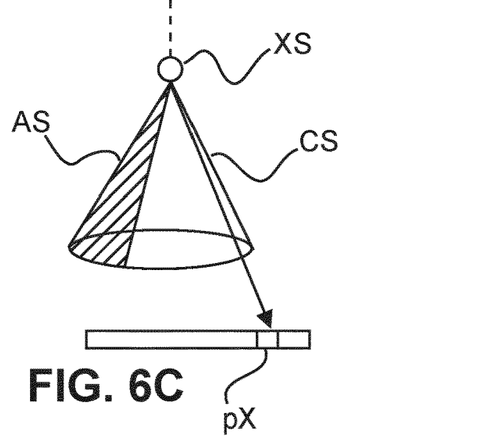

In another embodiment, illustrated in FIG. 6B, the rotation of the X-ray source around its rotation axis is used to effect this multi-spectral exposure. This embodiment is illustrated by a source XS rotation of 180° in between FIGS. 6B and 6C, with the anode side and the cathode side of the beam changing position. Due to the source rotation, geometrical pixel GR, measured at detector pixel PX, is exposed to anode side of the beam and hence to a first spectrum at one shot in imaging geometry as per FIG. 6B. In a next shot and after rotating the X-ray source by 90° or 180° as shown in FIG. 6C, the geometrical pixel GR (still measured at detector pixel PX) is now exposed to the cathode side of the beam to so receive photons at a second spectrum. The X-ray source can be rotated in angular steps of 90° or any other angular increment, each followed by a respective shot to ensure multi-spectral exposure of each geometrical pixel GR of interest. In this manner, pixel positions in a circular region around the rotation axis of the X-ray source will receive the multi-spectral exposure. However, this leaves a central portion around the rotation axis that does not necessarily receive such a multi-spectral exposure. To also cover these central pixels, the X-ray source and/or the patient may be subjected to a transversal motion such as is shown in FIG. 6A and the protocol as described in FIG. 6B,6C is then repeated to also expose the central pixels to sequential multi-spectral exposure.

Figure 6D:
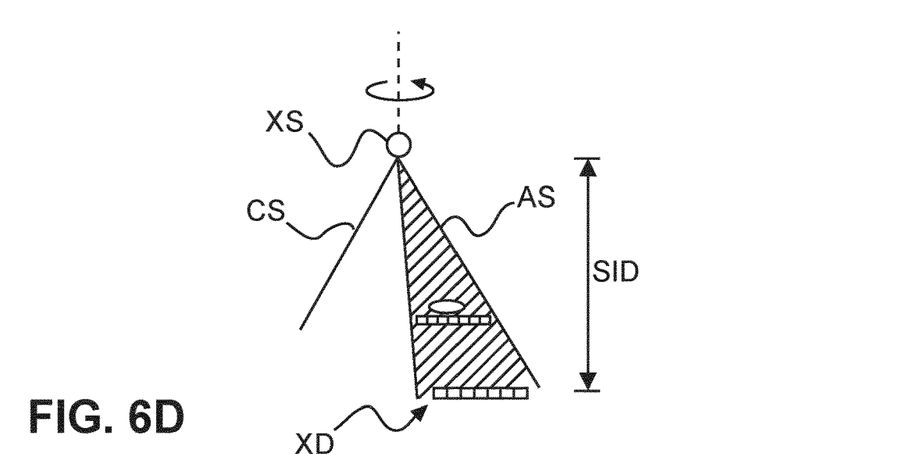

In another embodiment as shown in FIG. 6D, the diverging nature of the X-ray beam XB is exploited. To this end, the SID is made large enough so that the respective anode side and cathode side portions cover the whole, or at least the relevant part, of the X-ray detector plane XD. In this embodiment, sequential multi-spectral exposure of all or all relevant can be achieved in two shots, one for the anode side as shown in FIG. 6D, and another shot after rotation of the X-ray source as described in FIGS. 6B,C to the cathode side in a 180° rotation.

As mentioned, the there is no hard border for change of the spectrum from anode side AS to cathode side CS, but this change of spectra is gradual. However, for present purposes the portion of the beam that is inclined towards anode A and that corresponds to a take-off angle at least as large as the bevel angle of the anode may be considered the anode side whilst the remaining angular range can be considered the cathode side. Other definitions may be adopted so long as there is a sufficient difference between the two spectra.

Turning now to FIG. 7, this shows an extension of the above described embodiments where no additional hardware components are required. In this embodiment, there an additional FL component. However, this additional filter FL can be produced relatively cheaply and retro-fitting to existing imagers is easy to do at low cost.

Figure 7A:
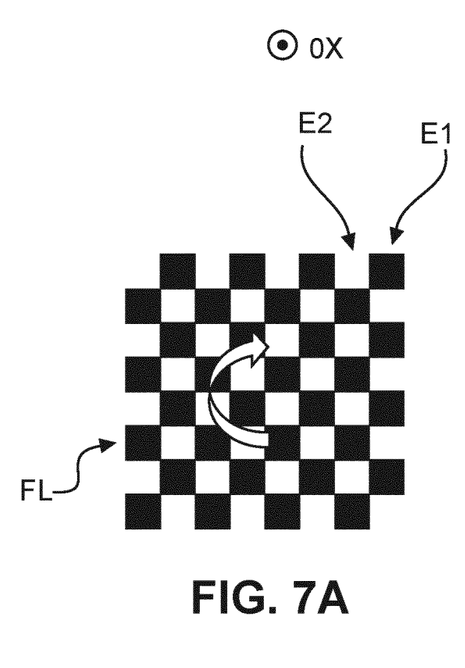
FIG. 7 shows a filter element for use in spectral imaging as envisaged herein.
Figure 7B:
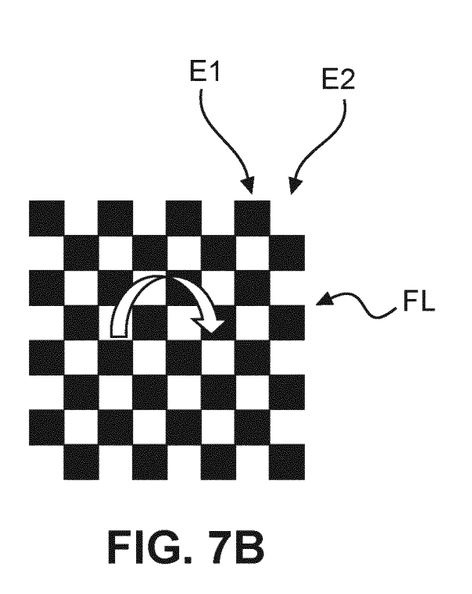

In the embodiments in FIG. 7A,B the additional hardware component, the filter element FL, includes at least different types of two sub-filter elements E1, E2, each type comprising a different material. The filter is essentially planar and may have any shape such as square, rectangular, or curved, such as spherical or other. Only two types of different material are required in layouts such as the one shown where a plurality of such element of the two types are arranged in layout with material type alteration. One dimensional (1D) or two dimensional (2D) designs are envisaged in embodiments. A 2D layout of one embodiment is shown in FIG. 7. Preferably the elements E1,E2 are arranged in a checkerboard pattern as shown in FIG. 7 although this is not necessary in all embodiments. In general, any two adjacent different filter sub-elements E1,E2 are made of different materials respectively. The filter elements may or may not have the same shape. The filter elements may not necessarily be of square shape but can be rectangular, round or of any other geometrical shape. Square or rectangular shapes are however preferred as they allow better coverage. The two materials E1, E2 are selected to cause different spectra. Suitable material combinations envisaged herein include Al (aluminium) and Cu (copper) or Al and Polyethylene.

One of the sub-elements may simply be implemented as an aperture thus leaving air as the other material. If the checker-board pattern as shown in FIGS. 7A,B is used, a rotation by 90° around a central axis (that extends into the drawing plane of FIG. 7) yields the two configurations in FIG. 7A, 7B. The rotation allows each pixel GR to be exposed in sequence to different spectra as induced by the respective filter elements E2, E1.

The rotation of the filter element occurs between shots and only two shots are required for this embodiment. The filter rotation may be administered by the control unit CU through a suitable actuator that rotates the filter around the rotation axis that passes through the layout plane of filter. The filter element is arranged between the X-ray source and the object OB. In particular, it can be arranged at the egress window EW after the collimator, if any. Each filter element E1, E2 is ensured to be in perspective registry with the respective pixel GR. In other words, each element E1 or E2 intersects a geometrical ray and is hence associated with the respective pixel GR further downstream.

Turning now in more detail to the signal processing by the spectral image processor SP it needs to be ensured that the correct spectral information is used for each pixel. A synchronizer (not shown) may operate shots for each shot by using information on the current imaging geometry to register the respective spectral exposure. In other words, the respective spectrum for each pixel and each shot is registered in a suitable data structure. The outcome of the synchronized read-out is two sets of projective spectral data $\pi 1$ and $\pi 2$. Each entry in one of the matrices corresponds to the intensity reading for one of the two spectra.

As mentioned earlier the transition of the spectra from cathode side to anode side is not a hard one but is gradual. Also, the spectra in the anode side of the beam XB differ with take-off angle. In other words, in the proposed scheme there is in general a range of respective anode side spectra rather than a single anode spectrum. However, for spectral imaging, the two spectra for each pixel GR should be known, at least in approximation up to an error bound. To account for this, different embodiments for the spectral image processing by a spectrum imaging processor SP are envisaged.

In one embodiment, the different spectra in the anode are simply averaged and each pixel is then assigned the same anode side spectrum, the same is done for the cathode side, although the cathode side is expected to be more homogeneous anyway.

This averaging may be suitable for simple spectral imaging tasks. The averaging may introduce some artifacts. In another embodiment, a theoretical spectral distribution model is used. In theory, because the material and the path length through the anode is known, and so is the imaging geometry, this model can be used to pre-compute the respective spectral pair for each pixel GR separately. In the previously mentioned case where the spectra information is averaged or in the case when each pixel is assigned a specific spectral pair based on the theoretical mode, the spectral imagery can be processed by classical, that is, analytical, spectral imaging algorithm as discussed Alvarez (mentioned above) where a system of linear equation is solved to compute the desired type of spectral imagery.

Instead of these explicit, analytic schemes, implicit scheme may be used instead, based on a machine learning model or algorithm. In this approach, a machine learning algorithm is used in which a model is trained based on previous data. One such model is a neural-network, in particular a convolutional neural-network CNN with one, or preferably more, hidden layers (deep learning).

Supervised learning may be used in which the training data includes pairs of training imagery, each pair including training input imagery and an associated target. The training input imagery includes two images acquired at different spectra or spectral characteristic and the target image is an associated true spectral image of the type one wishes to compute. The target may be a material map image. The spectral resolution may be better than the spectral resolution encounter during deployment (that is, after training of the machine learning model). In embodiments, the training input data may be generated from existing energy resolved projection data sets.

Different models may be trained for different types of spectral imagery. The training input imagery is fed into the model. Parameters of the model are adjusted based on the output of the model and the target. The parameters are adjusted to improve an objective function that measures a mismatch between output and target.

The training imagery may be produced by acquiring, in an experimental phase, the above described multi-spectral exposure images $\pi_{1,2}$ of a multi-material phantom such as a Shepp-Logan phantom. The neural-network is trained on true spectral images used as target to perform thickness estimation or material de-composition.

In embodiments, the phantom is first imaged by an imager with spectral imaging hardware (dual layer detector, dual X-ray source, fast switching X-ray sources, etc). The resulting imagery then forms the target for the training. The same phantom is then imaged using the above described heel-effect harnessing or filter FL-based imaging protocol to obtain the associated training input images. The heel-effect harnessing or filter FL-based imaging protocol may be run on a different, standard imager, or on the same spectral imager as used for the target, but without employing the spectral imaging hardware.

In a further embodiment, the target may be obtained as geometrically measured decompositions of a spectral phantom such as the Shepp-Logan phantom or other. Instead of using a real, physical, phantom, the training imagery may be partly or fully obtained through simulation.

The machine learning algorithm, such as the neural-network, once trained on true spectral imagery, is then able to compute in deployment from any new two sets of spectral projection imagery $\pi_1$ and $\pi_2$, a desired spectral image in image domain.

Using such a machine learning algorithm is advantageous as this approach does not require knowledge of the exact two spectra used for exposure for each geometrical pixel position. It is sufficient to simple have for each geometrical pixel two intensity readings at different spectra as obtainable by the above discussed heel effect harnessing protocol.

It should be further noted that with the above mentioned spectral scheme a traditional energy integrating image can also be produced. To this end the operator console may include the above mentioned user interface such as a button that allows the user to choose to operate the imager XI in traditional energy integrating mode or in the described spectral mode.

Figure 8:
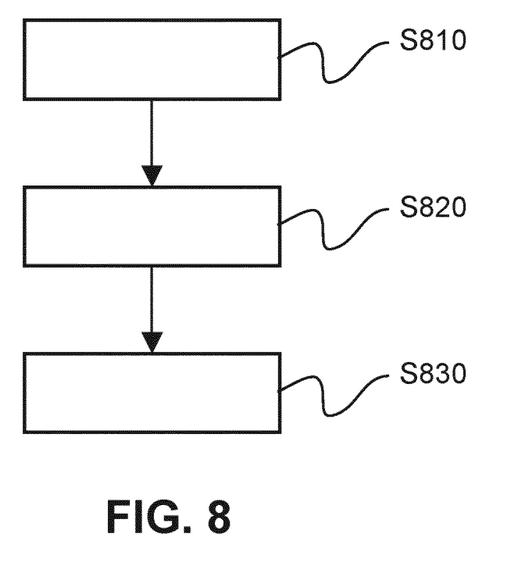
FIG. 8 shows a flow chart of a method of spectral imaging according to a first embodiment.

Reference is now made to FIG. 8 which shows a flow chart of a method for X-ray based spectral imaging to implement a protocol as discussed above in FIG. 6 where the heel effect is used. It will be understood however, that the below described computer implemented method steps are not necessarily tied to the architecture discussed above in FIGS. 1-6.

At step S810 a pixel, group of pixels or all pixels of the X-ray detector, are exposed to either an anode side or a cathode side of the X-ray beam. The anode side and the cathode side of the beam have different spectra due to the heel effect in the X-ray source used to generate the X-ray beam.

At step S820 an imaging geometry is changed so that the pixel or group of pixels is now exposed to the other side of the X-ray beam, that is the cathode or anode side, respectively.

Steps S810 and 820 are repeated so that all geometrical pixels of interest have received sequential multi-spectral exposure to anode side and cathode side of the X-ray beam.

At step S830 a spectral imaging algorithm is used to process the two sets of projection imagery obtained in steps S810 and S820. The so derived spectral imagery may then be processed or displayed or stored.

The proposed method may be used in projection domain as in planar radiography, but may also be used in tomographic imagery in imaging domain after a CT reconstruction from such projection imagery.

Figure 9:
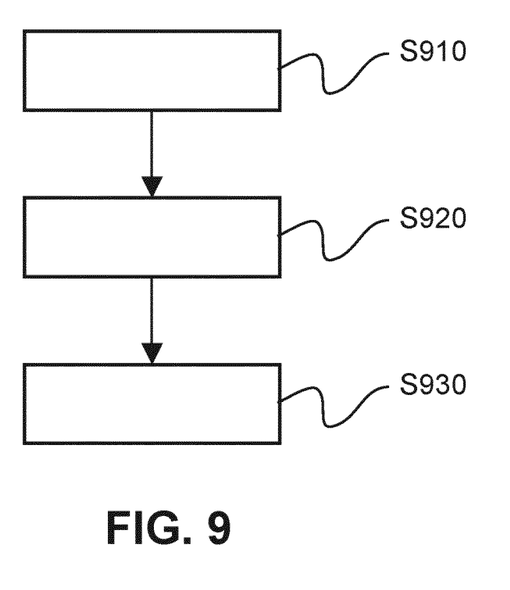
FIG. 9 shows a flow chart of a method of spectral X-ray imaging according to a second embodiment.

Reference is now made to the flow chart in FIG. 9 which represents the steps involved in using the multi-filter element filter FL described above in FIG. 7.

In this embodiment, at step S910 a pixel, a group of pixels or all pixels of an X-ray detector, are exposed to x-radiation after passage of the X-ray beam through a multi-element filter. The filter is arranged between the X-ray source and the object to be imaged. The filter includes at least two different filter elements made of different materials. The filter is moveable and is held in a first position so that the pixel or group of pixels is exposed to radiation at the first spectrum due to spectral modulation by elements of a first material type.

At step S920 the filter is then moved into a second position or configuration and exposure is repeated so that now, due to spectral modulation by the filter element(s) of the second type, the pixel or group of pixels is now exposed to radiation at a second spectrum.

At step S930 the two sets of projection images so obtained in steps S910 and S920 are then processed by a spectral imaging algorithm.

In embodiments of the two steps, different sub-elements of the filter of different material types are brought sequentially into respective registry with the geometrical pixel or group of pixels.

The motion to induce this change in spectra at step S920 can be rotational or transversal or both.

The filter may include exactly two elements of different materials and the filter is then scanned over the object. However, this is less preferably as this includes appreciable time delays.

Preferably, a checker-board based pattern is formed from a plurality of elements of at least two (in embodiments exactly two) different material (type) to cover the entire field of view. The motion can then be minimized and requires only a shift by one element, or a rotation by 90°, depending on the layout of the filter elements, to bring the two elements of two different material types into sequential registry with each geometrical pixel of interest.

The components of the image/signal processing sub-system SPS may be implemented as software modules or routines in a single software suit and run on a general purpose computing unit PU such as a workstation associated with the imager XI or a server computer associated with a group of imagers. Alternatively, the components of the image processing system SPS may be arranged in a distributed architecture and connected in a suitable communication network.

The control unit CU may be integrated in the operator console or may be remotely located therefrom. The control unit may be arranged in hardware or in software or in both. Preferably, the control unit CU may be implemented by re-programing an existing control unit of an imager XI to implement the above described heel effect harnessing protocol.

Alternatively, some or all components, including the control unit, may be arranged in hardware such as a suitably programmed FPGA (field-programmable-gate-array) or as hardwired IC chip.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:
1. An X-ray imaging apparatus, comprising:
an X-ray source comprising a cathode and an anode configured to generate an X-ray beam;
an X-ray detector configured to detect the X-ray beam after interaction with an imaged object, the X-ray beam having different spectra on an anode side and a cathode side caused by a heel effect when the X-ray source is in operation; and
a heel-effect-harnessing mechanism configured to cause a pixel of the X-ray detector to be alternately exposed to the anode side and the cathode side of the X-ray beam by changing an imaging geometry by controlling actuators in concert with a timing of read-out activity, the actuators acting on at least one of the X-ray source, a patient examination table, and the X-ray detector.

2. The X-ray imaging apparatus of claim 1, wherein the heel-effect-harnessing mechanism causes a relative motion between the object and the X-ray beam.

3. The X-ray imaging apparatus of claim 1, wherein the relative motion is caused by motion of at least a part of a support on which the imaged object resides during imaging, and/or or is caused by a motion of the X-ray source.

4. The X-ray imaging apparatus of claim 2, wherein the relative motion of the X-ray source is transversal and/or is rotatory so that respective positions of the anode and the cathode are changed.

5. The X-ray imaging apparatus of claim 1, wherein the heel-effect-harnessing mechanism causes a motion of the support and/or the X-ray source so as to increase a distance between the X-ray source and the object.

6. The X-ray imaging apparatus of claim 1, wherein a plurality of pixels is exposed to obtain two sets of intensity readings for the plurality of pixels, at least one for each of the two spectra, the X-ray apparatus further including a spectral imaging processor configured to compute spectral imagery for the object based one two sets of intensity readings.

7. A method for acquiring an image in an X-ray imaging apparatus, the method comprising:
providing an X-ray source comprising a cathode and an anode, the X-ray source being configured to generate an X-ray beam;
providing an X-ray detector configured to detect the X-ray beam after interaction with an imaged object, the X-ray beam having different spectra on an anode side and a cathode side caused by a heel effect when the X-ray source is in operation; and
alternately exposing a pixel of the X-ray detector to the anode side and the cathode side of the X-ray beam by changing a imaging geometry by controlling actuators in concert with a timing of read-out activity, the actuators acting on at least one of the X-ray source, a patient examination table, and the detector.

8. A method for acquiring an image in an X-ray imaging apparatus, the method comprising:
providing an X-ray source to generate an X-ray beam;
providing an X-ray detector configured to detect the X-ray beam after interaction with an imaged object; and
alternately exposing a pixel of the X-ray detector to the X-ray beam at first and second spectrum by moving a movable filter arranged between the X-ray source and the object so as to change at least locally a spectrum of the X-ray beam into the first and second spectrum.

9. The method as per claim 8, wherein two measurement values are detected at different spectra by alternately exposing the pixel, and further comprising processing the two measurement values by a spectral imaging algorithm.

10. The method as per claim 9, wherein the spectral imaging algorithm is implemented as a machine learning algorithm.

* * * * *